United States Patent [19]

Bowen et al.

[11] Patent Number: 4,918,175

[45] Date of Patent: Apr. 17, 1990

[54] BISMUTH (PHOSPH/SULF)ATED SACCHARIDES

[75] Inventors: S. Marc Bowen, Independence; Richard S. Bodine, Kansas City, both of Mo.; James C. Coleman, Lenexa, Kans.

[73] Assignee: Marion Laboratories, Inc., Kansas City, Mo.

[21] Appl. No.: 209,372

[22] Filed: Jun. 21, 1988

[51] Int. Cl.$^4$ .................. C07H 15/00; C07H 23/00; C07H 11/04; A61K 31/715
[52] U.S. Cl. .................................. 536/171; 536/121; 536/117
[58] Field of Search ............. 536/17.1, 121, 117; 514/53, 54

[56] References Cited

U.S. PATENT DOCUMENTS

| | | | |
|---|---|---|---|
| 3,379,717 | 4/1968 | Koopman et al. | 536/18.1 |
| 3,432,489 | 3/1969 | Nitta et al. | 536/121 |
| 3,838,150 | 9/1974 | Sugiura et al. | 536/121 |
| 4,581,221 | 4/1986 | Kuperus . | |

FOREIGN PATENT DOCUMENTS

| | | | |
|---|---|---|---|
| 107209 | 5/1984 | European Pat. Off. | 514/53 |
| 0136100 | 4/1985 | European Pat. Off. | 514/53 |
| 0230023 | 7/1987 | European Pat. Off. . | |
| 386562 | 1/1933 | United Kingdom | 536/121 |

OTHER PUBLICATIONS

Hall et al., Arch. Int. Pharmacodyn., 286, 308–19 (1987).
Windholz et al., (Eds.), The Merck Index, 10th Ed., Merck & Co., Inc. Rahway, N.J. (1983), p. 1273, entry no. 8755.
Berkow et al., (Eds.), The Merck Manual, 15th Ed., Merck Sharpe & Dohme Research Laboratories Div. of Merck & Co., Inc., Rahway, N.J. (1987), p. 744.
Barnhart et al. (Eds.), Physicians Desk Reference, 41st Ed., Medical Economics Co., Inc., Oradell, N.J. (1987), p. 1590.
Feldman, Am. J. Med. Sci., vol. 288 (3), 136–48 (1984), p. 144.
The Merck Index, 10th Ed., Ibid., pp. 177–180.
Anderson et al. (Eds.), Chem. Sources U.S.A., Directories Publishing Co., Inc., Ormond Beach, Fl. (1984), pp. 158, 257, 259, 262, 311, 326, 477 & 467.
Carey et al., Advanced Organic Chemistry, Part B: Reactions and Synthesis, Plenum Press, New York (1977), pp. 482–496 & 507.

*Primary Examiner*—Ronald W. Griffin
*Assistant Examiner*—Everett White
*Attorney, Agent, or Firm*—Christopher J. Rudy

[57] ABSTRACT

The titled compositions are useful as pharmaceuticals in ameliorating disorders associated with gastric mucosal damage. For example, compositions containing a complex salt of bismuth hydroxide sucrose octasulfate can be thus employed.

25 Claims, No Drawings

BISMUTH (PHOSPH/SULF)ATED SACCHARIDES

FIELD

This invention concerns bismuth phosphorylated and/or sulfonated saccharides, with procedures for preparation and use thereof. These saccharides in general are useful as pharmaceuticals.

BACKGROUND

Sucralfate is a well-known anti-ulcerative. See e.g., Windholz et al. (Eds.), *The Merck Index*, 10th Ed., Merck & Co., Inc., Rahway, N.J. (1983) at page 1273, entry no. 8755. See ref., Nitta et al., U.S. Pat. No. 3,432,489 (Mar. 11, 1968), which describes a disaccharide polysulfate aluminum compound and method.

Berkow et al. (Eds.), *The Merck Manual*, 15th Ed., Merck Sharpe & Dohme Research Laboratories Div. of Merck & Co., Inc., Rahway, N.J. (1987) at page 744 reports in regard to treatment of peptic ulcer that sucralfate is beneficial in treatment of all such ulcers, and several bismuth-containing preparations (including colloidal bismuth subcitrate) are effective in such treatment with an action similar to sucralfate.

Pepto Bismol ® is one well-known digestion aid having bismuth subsalicylate therein. See further, Barnhart et al. (Eds.), *Physicians' Desk Reference*, 41st Ed., Medical Economics Co., Inc., Oradell, N.J. (1987) at page 1590.

Feldman, *Am. J. Med. Sci.*, 288 (3), 136–48 (1984) at page 144 reports that the mechanism of action of bismuth subsalicylate is uncertain and that bismuth subcarbonate does not behave similarly thereto. This may suggest compound-specific action for bismuth-containing compositions.

*The Merck Index*, 10th Ed., ibid. at pages 177–80 reports on bismuth and some of its compounds. Bismuth, for example, is reported to have been used in viterinary medicine externally in dusting powders for indolent, moist or suppurating lesions, internally as a protecterant of the gastrointestinal lining and has been recommended to treat buccal (cheek) warts in dogs.

Michaeli, Eur. Pat. Appl. Pub. No 0 230 023 (July 29, 1987), discloses pharmaceutical compositions for the enhancement of wound healing. The compositions comprise sulfated saccharides, particularly mono- and disaccharides, or their salts, to enhance healing of wounds. Preferred salts are the soluble salts, most preferably the alkali metal salts, most particularly potassium and sodium salts. Sucrose octasulfate is the most preferred sulfated saccharide. The sacchardies may be present in any form, including liquids, gels or time-release polymers. In preferred practice the saccharide is present in combination with collagen.

Kuperus, U.S. Pat. No. 4,581,221 (Apr. 8, 1986), describes ulcer detection, with Tc-99m. Suitable ulcer-specific compounds for use therein include the metal or basic salts of maximally sulfated sucrose, etc. Lower molecular weight compounds are preferred for solubility and a quick gastrointestinal tract passage to leave the Tc-99m for the detection.

Kooperman et al., U.S. Pat. No. 3,379,717 (Apr. 23, 1968), describes bismuth subglycyrrhizinate and method of preparing same. The compound agrees with the formula $C_{41}H_{61}O_{14}COOBi$ and accelerates the healing of gastric ulcers.

SUMMARY

The present invention, ine one aspect, provides bismuth (phosph/sulf)ated saccharides. Another aspect provides a process for preparing a bismuth (phosph/sulf)ated saccharide comprising contacting a hydrogen (phosph/sulf)ated saccharide and a bismuth substance under conditions such that the bismuth (phosph/sulf)ated saccharide is prepared. A further aspect provides a method for ameliorating disorders associated with gastric mucosal damage of a subject comprising administering a bismuth (phosph/sulf)ated saccharide to the subject under conditions such that the gastric mucosal damage is treated.

The bismuth (phosph/sulf)ated saccharides are useful as pharmaceuticals. For instance, they are especially useful, in general, in the amolioration of such disorders associaed with gastric mucosal damage.

ILLUSTRATIVE DETAIL

In general, the bismuth (phosph/sulf)ated saccharides are compositions which contain such a component as bismuth. The bismuth saccharides of this invention further contain such a component as a phosphorylated and/or a sulfonated saccharide, which is a saccharide generally having more than one moiety selected from such moieties as at least one of phosphate and sulfate moieties esterified thereto.

The component such as bismuth includes such metallic elements as bismuth and pharmaceutically acceptable compounds therewith. The pharmaceutically acceptable compounds with bismuth include, of course, molecular level covalent or ionic complexes with bismuth and the phosphated and/or sulfated saccharide moieties, molecular level covalent or ionic complexes with such bismuth-containing moieties or compounds as bismuth hydroxides and the phosphated and/or sulfated saccharide moieties, these compositions in the presence of a suitable pharmaceutical carrier, and so forth and the like.

The component such as a sulfate ester and/or a phosphate ester saccharide includes thus such saccharides as (1) sulfated saccharides, (2) phosphated saccharides, (3) sulfated-phosphated saccharides, and (4) mixtures thereof. Saccharide components having at least three sulfate ester moieties per saccharide nucleus are desirably employed. Polysulfated saccharides are more typically employed in the practice of this invention. The polysulfated saccharides desirably contain substantial amounts of persulfated saccharides.

Saccharide moieties themselves which may be employed in the practice of this invention include mono-, di-, tri-, tetra- and oligosaccharides. Examples of suitable saccharide nuclei or moieties may be selected from appropriate residues of such saccharides as erythrose, threose, arabinose, deoxyribose, fructose, glucose, ribose, mannose, lactose, cellobiose, maltose, sucrose, trehalose, melezitose, stachyose, and so forth and the like. The saccharide moieties desirably are disaccharides of pentoses and/or hexoses. Sucrose is preferred.

The bismuth (phosph/sulf)ated saccharides may be a composite mixture, i.e., a composition combining more than one chemical entity to make up the composition. They may be considered complex bismuth salts of (phosph/sulf)ated saccharide(s).

The bismuth saccharides of this invention can be generally insoluble in water, lower alcohols, e.g., methanol, lower ketones, e.g., acetone, dilute aqueous hydrocloric acid, e.g., 0.1N, with generally no gelling propensity in acidic water. They may be semi-crystalline in the solid state.

Herein, a procedure is a method and/or process.

In general, the bismuth (phosph/sulf)ated saccharide can be prepared by contacting a hydrogen (phosph/sulf)ated saccharide and a bismuth substance. Conditions are those sufficient to form the bismuth saccharides of this invention.

In general, the hydrogen (phosph/sulf)ated saccharide is a saccharide analogous to that of the corresponding bismuth (phosph/sulf)ated saccharide but having phosphoric and/or sulfonic acid moieties bonded therewith. Sulfonic acids are preferred.

The hydrogen (phosph/sulf)ated saccharides can be obtained or can be prepared by known procedures or by procedures analogous thereto. For example, the following hydrogen (phosph/sulf)ated saccharides are in general commercially available:

2'-deoxy-α-D-ribose-1-phosphate;
2'-deoxyribose-5'-phosphate;
D-fructose-1-phosphate;
D-fructose-6-phosphate;
D-fructose-1,6-diphosphate;
α-D-galactose-1-phosphate;
D-galactose-6-phosphate;
galactose-6-sulfate;
glucose-1-phosphate;
D-glucose-1-phosphate;
glucose-6-phosphate;
D-glucose-6-phosphate;
glucose-1,6-diphosphate;
D-glucose-6-sulfate (sodium salt);
α-mannose-6-phosphate;
α-lactose-phosphate (barium salt).

See e.g., Anderson et al. (Eds.), *Chem Sources U.S.A.*, Directories Publishing Co., Inc., Ormond Beach, Fla. (1984). Also, phosphorylation and/or sulfonation may be accomplished on corresponding saccharides having appropriate esterfication site(s) available, as is known in the art. For example, phosphorylation may be accomplished by appropriate treatment of the reactant saccharide with a suitable phosphorylating agent, e.g., one which may be phosphoryl chloride or cyanoethyl phosphate. See e.g., Carey et al., *Advanced Organic Chemistry, Part B: Reactions and Synthesis,* Plenum Press, New York (1977) at pages 482–96 & 507. Sulfonation may be accomplished by appropriate treatment of the reactant saccharide with a suitable sulfating agent, e.g., chlorosulfonic acid, anhydrous sulfuric acid or sulfur trixodepyridine complex in a solvent such as pyridine, formamide, dimethyl formamide, chloroform or liquid sulfur dioxide. See e.g., Nitta et al., U.S. Pat. No. 3,432,489. See also, Michaeli, EP 0230023, especially for preparations with sodium and potassium sulfate saccharides.

Metal salts of the (phosph/sulf)ated saccharides may be converted to the hydrogen (phosph/sulf)ated saccharides by known procedures. For example, ion exchange procedures with an ion exchange resin such as a sulfonated divinyl benzene resin in its hydrogen ion form may be thus employed, passing the metal salts, desirably the potassium salts, over the resin in a suitable media, e.g., water, especially in a highly pure water in an about 20:1 weight-weight ratio of the water to metal salt, at room temperature in order to prepare the hydrogen (phosph/sulf)ated saccharides. The thus-prepared hydrogen (phosph/sulf)ated saccharides may be cooled to about 10° C. or so or ketp at temperatures about from 20° to 30° C. at this stage, if desired.

In general, the bismuth substance contains bismuth, which, when contacted with the hydrogen (phosph/sulf)ated saccharide, can form the bismuth (phosph/sulf)ated saccharide. As an illustration, the bismuth substance may be bismuth hydroxide ($Bi(OH)_3$). Freshly prepared $Bi(OH)_3$ is preferred. Commercially available $Bi(OH)_3$ may contain $Bi_2O_3$ and may not work as well in the practice of this invention.

Typically, the hydrogen (phosph/sulf)ated saccharide is dispersed or dissolved in a suitable medium, e.g., water, for the contact. Concentrations of the hydrogen (phosph/sulf)ated saccharide may vary widely, but higher aqueous concentrations, at accordingly low pH values, e.g., pH 1.5, may advantageously be employed. Temperatures can be about from 10° to 30° C., but may advantageously be about room temperature, e.g., about 25° C. The bismuth substance is contacted with the hydrogen saccharide dispersion or solution. Typically, the bismuth substance is a solid, and it may advantageously be stirred into the dispersion or solution of the hydrogen (phosph/sulf)ated saccharide, typically in water. Alternatively, for example, the bismuth substance may be slurried in water as a sample of fine particles, with the typically aqueous dispersion or solution of the hydrogen (phosph/sulf)ated saccharide being added thereto, e.g., slowly as from immediate prepartion from the mentioned ion exchange procedure using an ion exchange column. Amounts of the hydrogen (phosph/sulf)ated saccharide may advantageously be in a stoichiometric equivalent excess in comparison to the bismuth substance e.g., about from above 100 to 160 percent of theory or more in such an excess. Thus accordingly, e.g., the bismuth substance may be used in a molar ratio of about from 5:1 to 8:1 in comparison to the hydrogen (phosph/sulf)ated saccharide. Cooling during this contact step may be undertaken if desired, but it is not generally necessary if the contact is carried out at about room temperature. This mixture may be allowed to be stirred for a time, say, about from a score (20) minutes to an hour or so, e.g., about half an hour. The bismuth saccharide product is typically recovered as a solid.

The recovery of the product may advantageously be carried out by suction filtration and washing, with vacuum drying. The washing may generally be with such liquids as, e.g., water, methanol and/or acetone, etc. The product may be slurried in methanol and/or acetone and suction filtered therefrom if desired. Heating of the product to dry it should be avoided because temperatures above usual ambient temperatures, e.g., 45° C., may cause decomposition of the desired product. The product is thus advantageously stored under refrigeration, e.g., in a freezer, generally with cautionary protection from exposure to actinic radiation as may be provided with an amber or opaque glass bottle.

Yields of the product can be high. The yields can be as high as at least about 90 percent of theory or even about 95 percent of theory or more.

Procedures for use of the bismuth (phosph/sulf)ated saccharide generally involve treating gastric mucosal damage of a subject by orally administering an amount of the bismuth (phosph/sulf)ated saccharide effective to treat the damage. For instance, gastric mucosal damage may be the result of exposure to ethanol, excess acid and/or excess bile salts. Treatment of the gastric mucosal damage with the compositions of this invention ameliorates or even eliminates, the damage.

Suitable amounts of the bismuth (phosph/sulf)ated saccharide include those which may be in doses about from 5 to 100 mg per kg body weight of subject per dose, say, about 20 mg/kg/dose. Multiple doses per day are typical, often, say, four doses per day.

Dosage forms of the bismuth (phosph/sulf)ated saccharide may include such unit dosage forms as tablets, capsules and appropriate suspensions. Tablet forms may be advantageously employed because of ease of manufacture and administration.

Accordingly, numerous advantages attend this invention.

The following examples further illustrate the invention. Percentages are by weight unless otherwise specified.

EXAMPLE 1

To a 12-L 3-necked flask fitted with a mechanical stirrer and separatory/addition funnel was charged 1750 mL of glacial acetic acid and 3500 mL of "nanopure" water as obtained by passing deionized water through a NANOpure II (Barnstead) column. To the acid mixture was added 500 g of $Bi(NO_2)_3 \cdot 5H_2O$. The mixture was stirred to dissolve the solid. Next, with cooling, 3500 mL of concentrated (28%) $NH_4OH$ (aq.) was slowly added. The pH of the mixture became alkaline. Solid product was collected by filtration. The filtered solid was washed with "nanopure" water and next with methanol. The filtered solid was dried under vacuum at 50° C., which yielded 253.2 g of product $Bi(OH)_3$ (94.6 percent of theory).

A sample of 1600 g of Amberlite IR-120 ion exchange resin which had been washed with 2-3 bed volumes of 1N HCl (aq.) was loaded onto a column. The loaded resin was washed with "nanopure" water until the pH became nearly that of the water and until no chloride precipitate was observed with argentous nitrate.

A sample of 80 g of potassium sucrocose octasulfate ($K_8SOS$), which was previously prepared according to Exaples 1 & 2 of Michaeli, EP 0230023, was dissolved in about 1400 mL of "nanopure" water. This $K_8SOS$ solution was loaded onto the resin of the column and was eluted fairly rapidly with 4 L of "nanopure" water.

Effluent from the column was directed to a 12-L 3-necked flask containing a slurry of the above $Bi(OH)_3$ in 1 L of "nanopure" water. The slurry was cooled by an ice-water bath. The latter reaction mixture was next stirred for 30 minutes; whereupon it was filtered slowly with suction with several Buchner funnels. Suction was maintained overnight, and upon drying the product was ground to a finely divided state. The yield of product was 139.42 g (95.5 percent of theory). The product was odorless, white, semi-crystalline as determined by x-ray powder diffraction procedures, was insoluble in water, 0.1N HCl(aq.), methanol and acetone, was soluble in 4N sulfuric acid (aq.) and soluble in trifluoroacetic acid but decomposed gradually in these latter two acid media, and had the following composition:

Octasulfate content: 88.6 percent (HPLC & EA);
Heptasulfate content: 5.4 percent (HPLC & EA);
Hydroxide content as, e.g., $Bi(OH)_3$: 5.9 percent (HPLC & EA);
Bismuth content: 58.6 percent (AA & EA);
Water content: ca. 7.8 percent (Difference & Karl Fisher);
Microorganisms: None detected (Microbial bioburden).

The molecular structure was confirmed by Fourier transform infrared spectroscopy (FT-IR), by high pressure liquid chromatography (HPLC) against a known reference standard of $K_8SOS \cdot 7H_2O$ and by atomic absorbtion spectroscopy (AA). Elemental analyses (EA) were employed in the above. Thus, the product may be considered to be a complex salt of bismuth hydroxide sucrose octasulfate or substantially empirically $[Bi(OH)_2]_8SOS$.

EXAMPLE 2

The effectiveness of the $[Bi(OH)_2]_8SOS$ as from Example 1 as an antiulcer agent was determined by examining its actions in three animal models of gastric mucosal damage. Oral administration of 95% ethanol caused extensive gastric mucosal damage and the $[Bi(OH)_2]_8SOS$ was effective in reducing the severity of damage in this ethanol-induced gastric mucosal damage model. This model serves as a screen for antiulcer activity. Oral administration of 0.6M hydrochloric acid caused extensive gastric mucosal damage and the $[Bi(OH)_2]_8SOS$ was effective in reducing the severity in this hydrochloric acid-induced gastric mucosal damage model. This model also serves as a screen for antiulcer activity. When the pylorus is ligated (Shay rat model), gastric secretions accumulating over a time span of 14 hours caused extensive damage to the forestomach of the rat. The $[Bi(OH)]_8SOS$ was effective in reducing the severity of lesion induced in the Shay rat model. This model also serves as a screen for antiulcer activity.

Male Sprague-Dawley rats weighing approximately 200 g were used in these studies. They were maintained in individual hanging stainless steel cages, fasted for 48 hours prior to the start of the study and allowed free access to drinking water until the study commenced. The concentration of the $[Bi(OH)_2]_8SOS$ used in each study was 122.9 mg/mL IUPAC. The $[Bi(OH)_2]_8SOS$ was insoluble in deionized water and sonicaton was required for dosing. The $[Bi(OH)_2]_8SOS$ was administered orally in a volume of 1 mL via an oral dosing needle.

Determination of protective characteristics of the $[Bi(OH)_2]_8SOS$ against ethanol-induced gastric mucosal damage was undertaken. Rats were given 1 mL of the $[Bi(OH)_2]_8SOS$ orally fifteen minutes prior to oral administration of 1 mL of 95% ethanol. One hour later, stomachs were removed and the mucosal surface was examned macroscopically for damage. The degree of damage was graded according to the scale presented in Table 1 below.

TABLE 1

| \multicolumn{2}{c|}{GRADE OF OBSERVED MUCOSAL DAMAGE} |
|---|---|
| Grade | Appearance of Gastric Mucosa |
| 0 | Normal mucosa |
| 1 | Slight edema and congestion |
| 2 | Edema, congestion and bleeding |
| 3 | 1 or 2 spot erosions |
| 4 | 1 or 2 linear erosions |
| 5 | Many small and a few large erosions |
| 6 | Extensive erosions over entire mucosa |

Determination of protective characteristics of the $[Bi(OH)_2]_8SOS$ against hydrochloric acid-induced gastric musosal damage was undertaken. Rats were given 1 mL of the $[Bi(OH)_2]_8SOS$ orally fifteen minutes prior to oral administration of 1 mL of 0.6M hydrochloric acid.

One hour later, stomachs were removed, and the mucosal surface was examined macroscopically for damage. The degree of damage was again graded according to the scale presented in Table 1 above.

Determination of protective characteristics of the $[Bi(OH)_2]_8SOS$ in the Shay rat model was undertaken. Under ether anesthesia, the abdomen was opened, and the plyorus was ligated. Rats were immediately gven 1 mL of the $[Bi(OH)_2]_8SOS$; the abdomen was closed, and the animals were allowed to recover. Fourteen hours later, stomachs were removed and forestomachs were examined macroscopically for damage. The degree of damage was graded according to the scale presented in Table 2 below.

TABLE 2

| GRADE OF OBSERVED FORESTOMACH DAMAGE | |
|---|---|
| Grade | Appearance of Forestomach |
| 0 | Normal |
| 1 | Redness |
| 2 | One or two "spot" lesions |
| 3 | One or two "deep" lesions |
| 4 | Many, many deep lesions |

The results of the ethanol-induced gastric mucosal damage study are presented in Table 3 below. Treatment with 95% ethanol caused severe mucosal damage as seen in the water pretreatment control group where the mean grade of gastric mucosal damage was 4.78±0.26. The $[Bi(OH)_2]_8SOS$ pretreatment significantly reduced the severity of damage in this model to 3.10±0.48.

TABLE 3

| PROTECTION AGAINST 95% ETHANOL-INDUCED GASTRIC MUCOSAL DAMAGE | | |
|---|---|---|
| Pretreatment | Grade | N |
| Water | 4.78 ± 0.26 | 9 |
| $[Bi(OH)_2]_8SOS$ | 3.10 ± 0.48[1] | 10 |

[1]Significantly lower than the water-treated group $p < 0.05$

The results of the hydrochloric acid-induced gasric mucosal damage study are presented in Table 4 below. Treatment with 0.6M hydrochloric acid caused severe mucosal damage as seen in the water pretreatment control grop where the mean grade of gastric muscosal damage was 4.70±0.29. The $[Bi(OH)_2]_8SOS$ pretreatment significantly reduced the severity of damage in this model to 2.90±0.12.

TABLE 4

| PROTECTION AGAINST 0.6 M HYDROCHLORIC ACID GASTRIC MUCOSAL DAMAGE | | |
|---|---|---|
| Pretreatment | Grade | N |
| Water | 4.70 ± 0.29 | 10 |
| $[Bi(OH)_2]_8SOS$ | 2.90 ± 0.12[1] | 10 |

[1]Significantly lower than the water-treated group $p < 0.05$

The results of the Shay rat study are presented in Table 5 below. Ligation of the plyorus caused severe damage to the forestomach in 14 hours as seen in the water treatment control group where the mean grade of damage was 3.69±0.17. Treatmen wth the $[B(OH)_2]_8SOS$ significantly reduced the severity of damage in this model to 2.15±0.17. Note that seven of twenty (35%) of the rats in the water-treated control group died. The $[Bi(OH)_2]_8SOS$ treatment reduced mortality to 0% in this model.

TABLE 5

| PROTECTION IN THE SHAY RAT MODEL | | |
|---|---|---|
| Treatment | Grade | N |
| Water | 3.69 ± 0.17 | 13[2] |
| $[Bi(OH)_2]_8SOS$ | 2.15 ± 0.17[1] | 15 |

[1]Significantly lower than the water-treated group $p < 0.05$
[2]7 of 20 died.

Thus, the $[Bi(OH)_2]_8SOS$ proved to be effective in all three gastric mucosal damage models used in this study. Accordingly thus, the bismuth saccharides of this invention may be used in general for the treatment of peptic ulcers and/or gastritis in appropriate human subjects.

What is claimed is:

1. A bismuth (phosph/sulf)ated saccharide.
2. The compound of claim 1, which is a bismuth hydroxide sulfated saccharide.
3. The compound of claim 2, wherein saccharide moiety is a mono-, di-, tri- or tetrasaccharide.
4. The compound of claim 3, wherein saccharide moiety is a disaccharide, which is polysulfated.
5. The compound of claim 4, wherein saccharide moiety is substantially persulfated.
6. The compound of claim 5, wherein saccharide moiety is sucrose.
7. The compound of claim 1, which is a bismuth hydroxide (phosph/sulf)ated saccharide.
8. The compound of claim 1, which is a bismuth phosphated saccharide.
9. A complex salt of bismuth hydroxide sucrose octasulfate.
10. A process for preparing a bismuth (phosph/sulf)ated saccharide comprising contacting a hydrogen (phosph/sulf)ated saccharide and a bismuth substance under conditions such that the bismuth (phosph/sulf)ated saccharide is prepared.
11. The process of claim 10, wherein the bismuth substance is bismuth hydroxide.
12. The process of claim 10 wherein the bismuth (phosph/sulf)ated saccharide is a bismuth hydroxide (phosph/sulf)ated saccharide.
13. A method for ameliorating disorders associated with gastric mucosal damage of a subject comprising administering a bismuth (phosph/sulf)ated saccharide to the subject under conditions such that the gastric mucosal damage is treated.
14. The method of claim 13, wherein the gastric mucosal damage is substantially reduced.
15. The method of claim 14, wherein the bismuth (phosph/sulf)ated saccharide contains a complex salt of bismuth hydroxide sucrose octasulfate.
16. The method of claim 15, wherein the bismuth (phosph/sulf)ated saccharide is administered in an oral dosage form.
17. The method of claim 15, wherein the gastric mucosal damage results from exposure to ethanol, or excess acid or bile salts.
18. The method of claim 13, wherein the gastric mucosal damage is associated with at least one of a peptic ulcer and gastritis.
19. The method of claim 13, wherein the bismuth (phosph/sulf)ated saccharide is a bismuth hydroxide (phosph/sulf)ated saccharide.
20. The method of claim 13, wherein the bismuth (phosph/sul)ated saccharide is a phosphated saccharide.

21. A pharmaceutical composition comprising a bismuth (phosph/sulf)ated saccharide and a pharmaceutically acceptable carrier.

22. The composition of claim 21, which is in an oral dosage form.

23. The composition of claim 22, which contains a complex salt of bismuth hydroxide sucrose octasulfate.

24. The composition of claim 23, which is in a unit dosage form.

25. The composition of claim 21, which is a bismuth phosphated saccharide.

* * * * *